(12) United States Patent
Annby et al.

(10) Patent No.: US 6,515,152 B1
(45) Date of Patent: Feb. 4, 2003

(54) PROCESS FOR PRODUCTION OF AN OXETANE

(75) Inventors: Ulf Annby, Lund (SE); Nicola Rehnberg, Perstorp (SE)

(73) Assignee: Perstorp AB, Perstorp (SE)

( * ) Notice: Subject to any disclaimer, the term of this patent is extended or adjusted under 35 U.S.C. 154(b) by 0 days.

(21) Appl. No.: 09/868,031

(22) PCT Filed: Dec. 6, 1999

(86) PCT No.: PCT/SE99/02267

§ 371 (c)(1),
(2), (4) Date: Aug. 21, 2001

(87) PCT Pub. No.: WO00/35895

PCT Pub. Date: Jun. 22, 2000

(51) Int. Cl.$^7$ .................. C07D 305/14; C07D 305/06
(52) U.S. Cl. ........................... 549/510; 549/511
(58) Field of Search ................... 549/510, 511

(56) References Cited

FOREIGN PATENT DOCUMENTS

| | | |
|---|---|---|
| GB | 787406 | 12/1957 |
| JP | 107669 | 1/1998 |

OTHER PUBLICATIONS

STN International File CAPLUS accession No. 1995:785402, Document No. 123:227625, Mitsue Toatsu Chemicals: "Manufacture of dipentaerythritol", JP, A2.07165651, Jun. 27, 1995.

*Primary Examiner*—Ba K. Trinh
(74) *Attorney, Agent, or Firm*—Stevens, Davis, Miller & Mosher, L.L.P.

(57) ABSTRACT

A process for production of an oxetane, which process comprises subjecting an alcohol having two or more hydroxyl groups to reaction with a carbamide at a molar ratio employing 1–2 moles of said carbamide on 1–2 moles of said alcohol. The alcohols preferably have at least one 1,3-diol grouping. The reaction is carried out in the presence of at least one catalyst promoting and/or initiating transcarbonylation and/or pyrolysis. A reaction mixture comprising an oxetane and optionally an orthocarbonate of said alcohol is yielded. The oxetane is suitable recovered from said reaction mixture by for instance distillation.

32 Claims, No Drawings

PROCESS FOR PRODUCTION OF AN OXETANE

This application is a 371 of PCT/SE99/02267 dated Dec. 6, 1999.

The present invention refers to a novel, simple and inexpensive process for manufacture of an oxetane, which process provides technical as well as environmental advantages. The process includes subjecting an alcohol, having at least two hydroxyl groups, to a reaction with a carbamide compound in the presence of at least one catalyst.

Oxetanes as disclosed and produced by the process of the present invention are compounds having at least one four-membered ring of general formula (I)

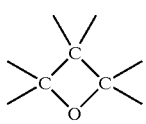

Formula (I)

Oxetanes have been prepared by a number of synthetic methods. The generally available methods include
- ring closure of 1,3-diol derivatives by the intramolecular Williamson reaction,
- decomposition of cyclic carbonate esters, and
- photochemical reaction of aldehydes and ketones with olefines.

The intramolecular Williamson reaction consists in general of the reaction of 1,3-halohydrins or their acetates with alkali. In 1878 trimethylene oxide, oxetane, was prepared for the first time by treating 3-chloropropanol with potassium hydroxide. 1,3-halohydrins and acetates thereof have since been widely used in the preparation of oxetanes. The use of acetate esters of said halohydrins often improves the oxetane yield. Hydrogen sulphate esters and sulphate esters are reported as replacements for 1,3-halohydrins in the intramolecular Williamson reaction. Mono (arenesulphonate) esters of 1,3-diols have also been used, especially for preparation of bicyclic oxetanes. Spiro-oxetanes have been prepared by treating di(phenylsulphates) with alkali.

Cyclic carbonate esters of diols decompose to oxetanes and carbon dioxide. The decomposition is normally carried at 160–260° C. in the presence of a basic catalyst.

Photochemical reaction of aldehydes and ketones with olefines (the so called Paterno-Büchi reaction) comprises generally that an olefine and an aldehyde or ketone are irradiated in an inert atmosphere by a high-pressure mercury lamp.

Further methods for preparation of oxetanes are disclosed in the patent literature, including British patent no. 787,406 disclosing a process for preparing oxetanes, which process comprises reacting a triol with a carbonic acid derivative of formula O=C(X)$_2$ wherein X is a halogen atom or an alkyloxy, cycloalkyloxy, aryloxy or tetrahydrofurfuryloxy radical. Compounds included in said formula are for instance phosgene, monoesters of chlorocarbonic acid and diesters of carbonic acid. The conversion proceeds in two stages and the reaction in respective step is dependent on employed carbonic acid derivative. The use of toxic and highly hazardous compounds such as phosgene renders the process a large number of disadvantages and drawbacks.

Japanese Unexamined Patent Publication HEI 10-7669 teaches a method for manufacturing an oxetane having a hydroxymethyl group. The method comprises causing a triol to react with an alkyl or alkylene carbonate yielding a cyclocarbonate compound which subsequently is decarboxylated in the presence of an alkaline catalyst The applicability of disclosed process is substantially limited by the fact that employed carbonates are too expensive for normal industrial use.

Oxetanes can, furthermore, be derived from other oxetanes by for instance electrolysis, oxidation over a silver catalyst, cyclisation by the Freund reaction or by substitution of halogen atoms.

Commonly used methods for preparation of oxetanes, the properties of prepared oxetanes as well as their polymerisation are thoroughly discussed in handbooks and encyclopaedias such as "*Encyclopedia of Polymer Science and Technology*", chapter "*Oxetane Polymers*", vol 9, 1968, pp 668–701, John Wiley & Sons Inc.

The present invention provides unexpectedly a novel, simple, inexpensive and reliable process for production of an oxetane, which process provides technical as well as environmental advantages. The process can be summarised by below simplified reaction scheme (I)

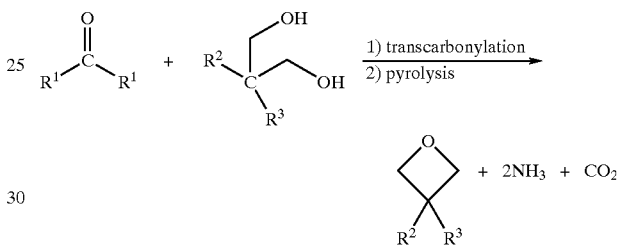

wherein $R^1$ is —NH$_2$ or —NR'R", wherein R' and R" is for instance hydrogen or alkyl, and wherein $R^2$ and $R^3$ may be a group such as alkyl, aryl or hydroxyalkyl. The process comprises subjecting an alcohol having two or more hydroxyl groups, which alcohol most preferably has at least one 1,3diol grouping, to a reaction with a carbamide at a molar ratio employing 1–2 moles of said carbamide on 1–2 moles of said alcohol, in the presence of at least one catalyst promoting and/or initiating transcarbonylation and/or pyrolysis. Preferred embodiments of the process of the present invention employ 1–1.2 mole of said carbamide on 1–1.8 mole of said alcohol. The reaction yields a reaction mixture comprising said oxetane, which subsequently is recovered by means of for instance distillation and/or extraction. The reaction is suitably performed in an inert atmosphere, such as nitrogen and/or argon atmosphere, and/or at a pressure of 0.01–1 bar, such as 0.1–0.5 bar. The reaction temperature is in preferred embodiments 100–250° C., such as 110–150° C. and/or 170–240° C. A suitable amount of catalyst is normally found within the range of 0.01–10 mole%, such as 0.5–2 mole%, calculated on moles of said alcohol, said carbamide and said catalyst. The reaction can also optionally be carried out in the presence of one or more solvents, such as an ethylene glycol, a propylene glycol, a butylene glycol, a hexanol, a heptanol, an octanol and/or a dodecanol. Suitable amount of said solvent is for instance 0.05–2, such as 0.1–1 or 0.2–0.5, moles on 1 mole of carbamide and alcohol.

A typical procedure can be exemplified as follows:

Carbamide and alcohol are mixed in for instance a molar ratio of 2:1 to 1:2, such as a 1:1 to 1:1.8, and at least one catalyst is added in the range of 0.01 to 10 mole %, such as 0.5 to 2 mole %, based on total moles of reactants and catalyst. Optionally, combinations of two or more catalysts can be used. The pressure in the reaction vessel is reduced to 0.01–1 bar, such as 0.1–0.5 bar. Optionally, a stream of an inert gas, such as nitrogen or argon, is passed through the vessel. The inert gas may be used combined with or instead of the reduced pressure. The temperature is then raised to 110–150° C., whereby a transcarbonylation starts. The temperature is preferably kept at 120–140° C. for 1 to 12 hours, such as 2 to 5 hours, or until the transcarbonylation is completed. A pyrolysis occurs subsequent to said transcarbonylation. The pressure is preferably reduced to 0.05 to 0.15 bar, such as 0.07 to 0.1 bar, and the temperature is slowly raised to 170 to 240° C., such as 180 and 200° C. The oxetane formed is suitably for instance continuously distilled off from yielded reaction mixture.

The preferred carbamide employed in the process of the present invention is as disclosed previously a compound of general formula (II)

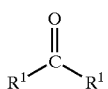

Formula (II)

wherein both substituents $R^1$ are $-NH_2$ or wherein each substituent $R^1$ independently is $-NR'R''$, wherein R' is hydrogen, linear or branched alkyl having for instance 1–12, such as 1–8, carbon atoms or is part of a bond between the nitrogen atoms in the two substituents R' thus being part of a ring formation, and wherein R'' is hydrogen or linear or branched alkyl having for instance 1–12, such as 1–8, carbon atoms. Carbamide is thus understood as for instance urea, N-alkylurea and N,N-dialkylurea. The preferred carbamide is urea, whereby the two substituents $R^1$ are $-NH_2$.

The alcohol reacted with said carbamide according to the process of the present invention is in preferred embodiments a compound of general formula (III)

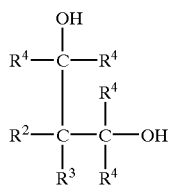

Formula (III)

wherein each $R^2$ and $R^3$ independently is alky, alkyloxy, alkyloxyalkyl, aryloxyalkyl, hydroxyalkyl, hydroxyalkyloxy, aryl or hydroxyaryl and wherein each $R^4$ independently is hydrogen or alkyl. Said alkyl is preferably linear or branched alkanyl or alkenyl having 1 to 24 such as 3–24, 1–12, 4–12 or 2–8, carbon atoms.

The alcohol is in the most preferred embodiments of the present invention selected from the group consisting of 2,2-dialkyl-1,3-propanediols, 2-alkyl-2-hydroxyalkyl-1,3-propanediols and 2,2-di(hydroxyalkyl)-1,3-propanediols and/or from the group consisting of dimers, trimers and polymers of said 1,3-propanediols. These alcohols can suitably be exemplified by neopentyl glycol, 2-methyl-2-propyl-1,3-propanediol, 2-ethyl-2-butyl-1,3-propanediol, trimethylolethane monoallyl ether, trimethylolpropane monoallyl ether, pentaerythritol diallyl ether, pentaerythritol monoallyl ether, trimethylolethane, trimethylolpropane, ditrimethylolethane, ditrimethylolpropane, pentaerythritol, dipentaerythritol, tripentaerythritol and esters of dimethylolpropionic acid. Further preferred embodiments include selectively alkoxylated 1,3-propanediols such as 2-alkyl-2-hydroxyalkoxy-1,3-propanediols, 2,2-di(hydroxyalkyloxy)--1,3-propanediols, wherein alkyloxy is linear or branched having for instance 3–24, such as 4–12 carbon atoms, or selectively alkoxylated dimers, trimers or polymers thereof Said selectively alkoxylated 1,3-propanediols can be exemplified by selectively ethoxylated and/or propoxylated trimethylolethane, trimethylolpropane, pentaerythritol, ditrimethylolethane, ditrimethylolpropane, dipentaerythritol or tripentaerythritol. A selectively alkoxylated 1,3-propanediol or dimer, trimer or polymer thereof as disclosed above is understood as a derivative wherein the hydroxyl groups of the 1,3-diol grouping are non-alkoxylated.

Alkoxylated alcohols can be obtained by reacting at least one alcohol with at least one alkylene oxide, such as ethylene oxide, propylene oxide and/or butylene oxide. A suitable alkoxylation degree is for instance 0.5–10, that is 0.5–10 moles of said alkylene oxide on 1 mole of said alcohol. Selectively alkoxylated alcohols are for instance obtained from triols, tetrols and higher alcohols having for instance a 1,3-diol grouping of formula (III) wherein $R^2$ and/or $R^3$ are for instance hydroxyalkyl. The hydroxyl groups of the 1,3-diol grouping of said formula (I) are before alkoxylation protected and subsequent said alkoxylation deprotected. A suitable protection method is for instance acetal formation. Further suitable protection and deprotection methods are disclosed in for instance "Protective Groups in Organic Synthesis" chapter 2 "Protection for the Hydroxyl Group, Including 1,2- and 1,3-diols" by Theodora W. Greene and Peter G. M. Wuts, John Wiley & Sons 1991.

The catalyst used in preferred embodiments of the present invention can suitably be exemplified by KOH, $K_2CO_3$, NaOH, $Na_2CO_3$, LiOH, $Li_2CO_3$, KH, NaH, LiH, $KNH_2$, $NaNH_2$, $LiNH_2$, $MgCO_3$, $Sr(OH)_2$, $Zn(OH)_2$, $Zn(OR)_2$ wherein OR is alkoxide having 1 to 4 carbon atoms, elemental Na, elemental Li, $2-N(R)_2$-pyridine or $4N(R)_2$-pyridine wherein R is hydrogen or $C_1-C_{18}$ alkyl, trialkylamines, triarylphospine, ZnO, Zn(II)acetate, $Zn(O_2CR)_2$ wherein R is $C_2-C_{17}$ hydrocarbyl, $Zn(X)_2$ wherein X is F, Cl, Dr or I, $Bu_2SnO$ or $Bu_2Sn(OR)_2$ wherein Bu is butyl and OR is alkoxide having 1 to 4 carbon atoms, $Ti(OR)_4$ or $Zr(OR)_4$ wherein OR is alkoxide having 1 to 4 carbon atoms, $Ti(X)_4$ or $Zr(X)_4$ wherein X is F, Cl, Br or I, $AlH(R)_2$ wherein R is $C_1-C_{12}$, $AlCl_3$, $FeCl_3$ or Fe(III)acetylacetonate or is a combination of two or more of said compounds.

The oxetane yielded and recovered from the process of the present invention is in the most preferred embodiments a compound of general formula (IV)

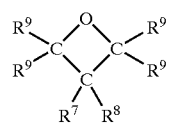

Formula (IV)

wherein each $R^7$ and $R^8$ independently is alkyl, alkyloxy, alkyloxyalkyl, aryloxyalkyl, hydroxyalkyl, hydroxyalkyloxy, aryl or hydroxyaryl and wherein each $R^9$ independently is hydrogen or alkyl. Said alkyl preferably is linear or branched alkanyl or alkenyl having 1–24, such as 3–24, 1–12, 4–12 or 2–8, carbon atoms. Substituents $R^7$ and $R^8$ can optionally and where applicable suitably comprise one or more oxetane rings of formula (I). The oxetane is in especially preferred embodiments an oxetane of trimethylolethane, trimethylolpropane, pentaerythritol, ditrimethylolethane, ditrimethylolpropane or dipentaerythritol or is an oxetane of a selectively alkoxylated, such as said ethoxylated and/or propoxylated, trimethylolethane, trimethylolpropane, pentaerythritol, ditrimethylolethane, ditrimethylolpropane or dipentaerythritol. Selectively alkoxylated is interpreted and suitably exemplified as disclosed previously, whereby said oxetane in these embodiments preferably is an oxetane of a 2-alkyl-2-hydroxyalkyloxy-1,3-propanediol, a 2,2-di(hydroxyalkyloxy)-1,3-propanediol or a dimer, trimer or polymer of said 1,3-propanediol Said alkyloxy is as previously disclosed preferably linear or branched having 3–24, such as 4–12, carbon atoms.

The reaction mixture yielded from the reaction, included in the process of the present invention, between carbamide and alcohol may in addition to said oxetane comprise an orthocarbonate of said alcohol as reaction by-product. Conditions and molar ratio in the process of the present invention may be varied to obtain an orthocarbonate of general formula (V)

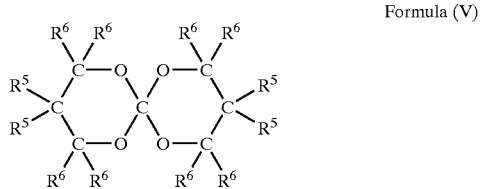

Formula (V)

wherein each $R^5$ independently is alkyl, alkyloxy, alkyloxyalkyl, aryloxyalkyl, hydroxyalkyl, hydroxyalkyloxy, aryl or hydroxyaryl and wherein each $R^6$ independently is hydrogen or alkyl. Said alkyl is preferably linear or branched alkanyl or alkenyl having 1–24, such as 3–24, 1–12, 4–12 or 2 to 8, carbon atoms. The orthocarbonate may be recovered by methods such as recrystallisation, distillation, extraction, chromatography and the like, and optionally decomposed, such as hydrolysed under acidic conditions, whereby at least said alcohol is yielded, recovered and preferably recirculated for reaction with carbamide in accordance with the process of the present invention. In cases where conditions are chosen to allow formation of considerable amounts of the orthocarbonate this may either be separated from yielded reaction mixture and recovered as a separate product, or may as disclosed above be hydrolysed to original alcohol and used to repeat the process after addition of a proper amount of carbamide.

These and other objects and the attendant advantages will be more fully understood from the following detailed description, taken in conjunction with embodiment Examples 1–9.

Examples 1–6, 11 and 12 refer to syntheses in accordance with embodiments of the present invention, yielding an oxetane and in Examples 1–4, 11 and 12 a spiro-orthocarbonate as by-product.

Example 7 refer to NMR characterisation of the oxetane obtained in Examples 1–6.

Example 8 refer to NMR characterisation of the by-product obtained in Examples 1–4.

Example 9 refer to hydrolytic decomposition of the spiro-orthocarbonate obtained in Example 3.

Example 10 refer to synthesis of an oxetane using the alcohol obtained from the decomposition of the spiro-orthocarbonate of Example 9.

EXAMPLE 1

170 moles of urea and 171 moles of a commercially available trimethylolpropane (TMP, Perstorp Polyols) were together with 1.5 mole % of zinc(II)acetate and 2 mole % of potassium hydroxide (both based on total amount of reactants and catalysts) charged in a reaction vessel. The pressure was reduced to 0.4 bar and the mixture heated to 140° C. for transcarbonylation. The temperature was maintained under stirring for 5 hours. The pressure was, following the transcarbonylation, decreased to 0.05–01 bar and the temperature was under vigorous stirring slowly raised to 195° C. yielding in a pyrolysis 92.1 moles of 3-ethyl-3-hydroxymethyloxetane (trimethylolpropane oxetane). The oxetane was distilled off as it formed and collected for NMR characterisation (see Example 7). 23.9 moles of spiro-orthocarbonate was yielded as by-product. The spiro-orthocarbonate was also collected and NMR characterised (see Example 8).

EXAMPLE 2

418 moles of urea and 507 moles of trimethylolpropane (TMP, Perstorp Polyols) were together with 1.5 mole % of zinc(II)acetate and 2 mole % of potassium hydroxide (both based on total amount of reactants and catalysts) charged in a reaction vessel. The pressure was reduced to 0.4 bar and the mixture heated to 140° C. for transcarbonylation. The temperature was maintained under stirring for 5 hours. The pressure was, following the transcarbonylation, decreased to 0.05–01 bar and the temperature was under vigorous stirring slowly raised to 195° C. yielding in a pyrolysis 213 moles of 3-ethyl-3-hydroxymethyloxetane (trimethylolpropane oxetane). The oxetane was distilled off as it formed and collected for NMR characterisation (see Example 7). 49.9 moles of spiro-orthocarbonate was yielded as by-product. The spiro-orthocarbonate was also collected and NMR characterised (see Example 8).

EXAMPLE 3

416 moles of urea and 346 moles of trimethylolpropane (1.%P, Perstorp Polyols) were together with 1.5 mole % of zinc(II)acetate and 2 mole % of potassium hydroxide (both based on total amount of reactants and catalysts) charged in a reaction vessel. The pressure was reduced to 0.4 bar and the mixture heated to 140° C. for transcarbonylation. The temperature was maintained under stirring for 5 hours. The pressure was, following the transcarbonylation, decreased to 0.05–01 bar and the temperature was under vigorous stirring slowly raised to 195° C. yielding in a pyrolysis 173 moles of 3-ethyl-3-hydroxymethyloxetane (trimethylolpropane oxetane). The oxetane was distilled off as it formed and collected for NMR characterisation (see Example 7). 86.5 moles of spiro-orthocarbonate was yielded as by-product. The spiro-orthocarbonate was collected, NMR characterised (see Example 8) and hydrolytically decomposed (see Example 9).

EXAMPLE 4

416 moles of urea and 346 moles of trimethylolpropane (TMP, Perstorp Polyols) were together with 1.5 mole % of zinc(II)acetate and 2 mole % of potassium hydroxide (both based on total amount of reactants and catalysts) charged in a reaction vessel. The pressure was reduced to 0.4 bar and the mixture heated to 140° C. for transcarbonylation. The temperature was maintained under stirring for 1.5 hours. The pressure was, following the transcarbonylation, decreased to 0.05–01 bar and the temperature was under vigorous stirring slowly raised to 195° C. yielding in a pyrolysis 168 moles of 3-ethyl-3-hydroxymethyloxetane (trimethylolpropane oxetane). The oxetane was distilled off as it formed and collected for NMR characterisation (see Example 7). The amount of unreacted trimethylolpropane was determined to 190 moles and the major constituent of this remainder was spiro-orthocarbonate. The spiro-orthocarbonate also was collected and NMR characterised (see Example 8).

EXAMPLE 5

335 moles of urea and 663 moles of trimethylolpropane (TMP, Perstorp Polyols) were together with 1.5 mole % of zinc(II)acetate and 2 mole % of potassium hydroxide (both based on total amount of reactants and catalysts) charged in a reaction vessel. The pressure was reduced to 0.4 bar and the mixture heated to 140° C. for transcarbonylation. The temperature was maintained under stirring for 5 hours. The pressure was, following the transcarbonylation, decreased to 0.05–01 bar and the temperature was under vigorous stirring slowly raised to 195° C. yielding in a pyrolysis 198 moles of 3-ethyl-3-hydroxymethyloxetane (trimethylolpropane oxetane). The oxetane was distilled off as it formed and collected for NMR characterisation (see Example 7). The amount of unreacted trimethylolpropane was determined to 465 moles.

EXAMPLE 6

335 moles of urea and 663 moles of trimethylolpropane (TM?, Perstorp Polyols) were together with 1.5 mole % of zinc(II)acetate and 2 mole % of potassium hydroxide (both based on total amount of reactants and catalysts) charged in a reaction vessel. The pressure was reduced to 0.4 bar and the mixture heated to 140° C. for transcarbonylation. The temperature was maintained under stirring for 1.5 hours. The pressure was, following the transcarbonylation, decreased to 0.05–01 bar and the temperature was under vigorous stirring slowly raised to 195° C. yielding in a pyrolysis 214 moles of 3-ethyl-3-hydroxymethyloxetane (trimethylolpropane oxetane). The oxetane was distilled off as it formed and collected for NMR characterisation (see Example 7). The amount of unreacted trimethylolpropane was determined to 449 moles.

EXAMPLE 7

The oxetane yielded in Examples 1–6 was NMR characterised to evidence that 3-ethyl-3-hydroxymethyloxetane (trimethylolpropane oxetane) was the product obtained.

Result: $^1$H NMR (CDCl$_3$): δ4.47, 4.41 (4H, CH$_2$OCH$_2$, two d); 3.75 (2H, CH$_2$OH, d), 2.90 (1H, OH, t); 1.73 (2H, q); 0.90 (3H, t) $^{13}$C NMR(CDCl$_3$): δ78.46; 65.63; 44.70; 26.58; 8.58

EXAMPLE 8

The spiro-orthocarbonate yielded in Examples 1–4 as by-product was NMR characterised, which evidenced the product to be 3,9-diethyl-3,9-bis(hydroxymethyl)-1,5,7,11-tetraoxaspiro[5.5]undecane, that is the spiro-orthocarbonate of trimethylolpropane.

Result: $^1$H NMR (CDCl$_3$): δ3.89–3.69 (12 H, m, CH$_2$O); 1.60 (2H, br, OH); 1.36 (4H, q); 0.85(6H, t). $^{13}$C NMR (CDCl$_3$): δ115.0 (C$_q$—O); 67.70, 67.24 and 61.89 (C—O); 37.02 (C$_q$); 23.44; 7.55. HETCOR analysis confirmed assignments. MS (CI): 277 (M$^+$+1); 161 (M$^+$+1-TMPO). HRMS (CI): observed 277.1674, calculated 277.1651 for C$_{13}$H$_{25}$O$_6$. 161.0815, calculated 161.0814 for C$_7$H$_{13}$O$_4$. FTIR (KBr): cm$^{-1}$ 3569 (s sharp, OH); 3500–3100 (s, broad, OH); 1188, 1017 (s, COC).

EXAMPLE 9

24.7 g of the spiro-orthocarbonate obtained in Example 3 and characterised in Example 8 was mixed with 150 ml of water and 5 g of hydrochloric acid (36-w/w HCl). The mixture was heated to 100° C. for 60 minutes and subsequently evaporated in vacuum. The remainder after said evaporation consisted of 24 g of essentially pure trimethylolpropane.

EXAMPLE 10

Example 1 was repeated with the difference that the commercially available trimethylolpropane was replaced by trimethylolpropane obtained as in Example 9, whereby ca. 92 moles of 3-ethyl-3-hydroxymethyloxetane (trimethylolpropane oxetane) and ca 24 moles of spiro-orthocarbonate as by-product was yielded.

EXAMPLE 11

402 mmoles of trimethylolethane and 335 mmoles of carbamide were together with 1.1 mole % of potassium hydroxide (based on total amount of reactants and catalysts) charged in a reaction vessel. The synthesis was performed in accordance with Example 1. 60 mmoles of 3-hydroxymethyl-3-methyloxetane (trimethylolethane oxetane) was yielded from the distillate and characterised by NMR. The remainder contained the spiro-orthocarbonate yielded as by-product.

EXAMPLE 12

84.5 mmoles of trimethylolhexane and 70.9 mmoles of carbamide were together with 1.2 mole % of potassium hydroxide (based on total amount of reactants and catalysts) charged in a reaction vessel. The synthesis was performed in accordance with Example 1. The temperature uring the pyrolysis gradually raised to 215° C. 20.6 mmoles of 3-hydroxymethyl-3-pentyloxetane (trimethylolhexane oxetane) was yielded from the distillate and characterised by NMR. The remainder contained the spiro-orthocarbonate (3% on the carbamide) yielded as by-product.

While particular embodiments of the invention have been shown, it will be understood, of course, that the invention is not limited thereto since many modifications may be made, and it is, therefore, contemplated to cover by the appended claims any such modifications as fall within the true spirit and scope of the invention.

What is claimed is:

1. A process for production of an oxetane, which process comprises subjecting an alcohol having two or more hydroxyl groups to reaction with a carbamide, at a molar ratio employing 1 to 2 moles of said carbamide on 1 to 2 moles of said alcohol and in the presence of at least one catalyst promoting and/or initiating transcarbonylation and/or pyrolysis, whereby a reaction mixture comprising at least one oxetane, and optionally at least one orthocarbonate, of said alcohol is yielded, and wherein said oxetane and optionally said orthocarbonate is recovered from said reaction mixture.

2. A process according to claim 1, wherein 1 to 1.2 mole of said carbamide is employed on 1 to 1.8 mole of said alcohol.

3. A process according to claim 1, wherein said carbamide is a compound of general formula (H)

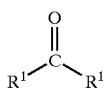

Formula (II)

wherein R' is —NH2 or wherein each $R^1$ independently is —NR'R", wherein R' is part of a bond between respective nitrogen atom in substituents $R^1$, hydrogen or alkyl and wherein R' is hydrogen alkyl.

4. A process according to claim 3, wherein said alkyl is linear or branched alkanyl or alkenyl having 1 to 12, such as 1 to 8, carbon atoms.

5. A process according to claim 3, wherein $R^1$ is —$NH_2$, whereby said carbamide is urea.

6. A process according to claim 1, wherein said alcohol has at least one 1,3-diol grouping.

7. A process according to claim 1, wherein said alcohol is an alcohol of general formula (III)

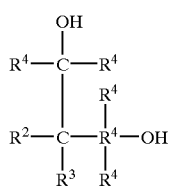

Formula (III)

wherein each $R^2$ and $R^3$ independently is alkyl, alkyloxy, alkyloxyalkyl, aryloxyalkyl, hydroxyalkyl or hydroxyalkyloxy, aryl or hydroxyaryl and wherein each $R^4$ independently is hydrogen or alkyl.

8. A processing according to claim 1, wherein said alcohol is a 2,2-dialkyl-1,3-propanediol, a 2-alkyl-2-hydroxyalkyl-1,3-propanediol, a 2,2-di(hydroxyalkyl)-1,3-propanediol or a dimer, trimer or polymer of said 1,3-propanediol.

9. A process according to claim 7, wherein said alkyl is linear or branched alkanyl or alkenyl having 1 to 24, such as 3 to 24, 1 to 12, 4 to 12 or 2 to 8, carbon atoms.

10. A process according to claim 1, wherein said alcohol is neopentyl glycol, 2-methyl-2-propyl-1,3-propanediol, 2-ethyl-2-butyl-1,3-propanediol, trimethylolethane monallyl ether, trimethylolpropane monoallyl ether, pentaerythritol diallyl ether, pentaerythritol monoallyl ether, trimethylolethane, trimethylolpropane, ditrimethylolethane, ditrimethylolpropane, pentaerythritol, dipentaerythritol or tripentaerythritol.

11. A process according to claim 1, wherein said alcohol is a 2-alkyl-2-hydroxyalkyloxy-1,3-propanediol, a 2,2-di(hydroxyalkyloxy)-1,3-propanediol or a dimer, trimer or polymer of said 1,3-propanediol.

12. A process according to claim 11, wherein said alkyloxy is linear or branched having 3 to 24, such as 4 to 12, carbon atoms.

13. A process according to claim 1, wherein said reaction is performed at a temperature of 100 to 250° C., such as 110 to 150° C. and/or 170 to 240° C.

14. A process according to claim 13, wherein said temperature is applied in two or more steps, whereby a first temperature of 110 to 150° C., preferably 120 to 140° C., and a final temperature of 170 to 240° C., preferably 180 to 200° C., are applied.

15. A process according to claim 1, wherein said reaction is performed at a pressure of 0.01 to 1 bar, such as 0.1 to 0.5 bar.

16. A process according to claim 1, wherein said reaction is performed in an inert atmosphere, such as nitrogen and/or argon atmosphere.

17. A process according to claim 1, wherein said reaction is performed in the presence of at least one solvent.

18. A process according to claim 17, wherein said solvent is an ethylene glycol, a propylene glycol, a butylene glycol, pentanol, a hexanol, a heptanol, an octanol and/or a dodecanol.

19. A process according to claim 17, wherein said solvent is added in an amount corresponding to 0.05 to 2, such as 0.1 to 1 or 0.2 to 0.5, moles on 1 mole of said carbamide and said alcohol.

20. A process according to claim 1, wherein said catalyst is employed in an amount of 0.01 to 10 mole %, preferably 0.5 to 2 mole %, calculated on subtotal moles of said alcohol, said carbamide and said catalyst.

21. A process according to claim 1, wherein said catalyst is KOH, $K_2CO_3$, NaOH, $Na_2CO_3$, LiOH, $Li_2CO_3$, KH, NaH, LiH, $KNH_2$, $NaNH_2$, $LiNH_2$, $MgCO_3$, $Sr(OH)_2$, $Zn(OH)_2$, $Zn(OR)_2$ wherein OR is alkoxide having 1 to 4 carbon atoms, elemental Na, elemental Li, 2-$N(R)_2$-pyridine or 4-$N(R)_2$-pyridine wherein R is hydrogen or $C_1$–$C_{18}$ alkyl, trialkylamines, triarylphospine, ZnO, Zn(II)acetate, $Zn(O_2CR)_2$ wherein R is $C_2$–$C_7$ hydrocarbyl, $Zn(X)_2$ wherein X is F, Cl, Br or I, $Bu_2SnO$ or $Bu_2Sn(OR)_2$ wherein Bu is butyl and OR is alkoxide having 1 to 4 carbon atoms, $Ti(X)_4$ or $Zr(X)_4$ wherein X is F, Cl, Br or I, $AlH(R)_2$ wherein R is $C_1$–$C_{12}$, $AlCl_3$, $FeCl_3$ or Fe(III)acetylacetonate or is a combination of two or more of said compounds.

22. A process according to claim 1, wherein said oxetane is a compound of general formula (IV)

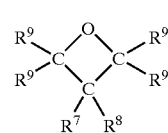

Formula (IV)

wherein each $R^7$ and R8 independently is alkyl, alkyloxy, alkyloxyalkyl, aryloxyalkyl, hydroxyalkyl or hydroxyalkyloxy, aryl or hydroxyaryl and wherein each $R^9$ independently is hydrogen or alkyl.

23. A process according to claim 22, wherein, said alkyl is linear or branched alkanyl or alkenyl having 1 to 24, such as 3 to 24, 1 to 12, 4 to 12 or 2 to 8, carbon atoms.

24. A process according to claim 1, wherein said oxetane is an oxetane of trimethylolethane, trimethylolpropane, pentaerythritol, ditrimethylolethane, ditrimethylolpropane or dipentaerythritol.

25. A process according to claim 1, wherein said oxetane is an oxetane of a 2-alkyl-2-hydroxyalkyloxy-1,3-propanediol, a 2,2-di(hydroxyalkyloxy)-1,3-propanediol or a dimer, trimer or polymer of said 1,3-propanediol.

26. A process according to claim 25, wherein said alkyloxy is linear or branched having 3 to 24, such as 4 to 12, carbon atoms.

27. A process according to claim 1, wherein said oxetane is recovered from said reaction mixture by distillation.

28. A process according to claim 1, wherein said reaction mixture yielded from said reaction between carbamide and alcohol comprises said orthocarbonate of said alcohol.

29. A process according to claim 28, wherein said orthocarbonate is recovered and optionally decomposed under acidic conditions, whereby at least said alcohol is yielded, recovered and recirculated for reaction with said carbamide.

30. A process according to claim 28, wherein said orthocarbonate is a compound of general formula (V)

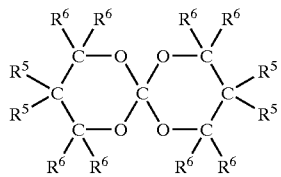

Formula (V)

wherein each $R^5$ independently is alkyl, alkyloxy, alkyloxyalkyl, aryloxyalkyl, hydroxyalkyl or hydroxyalkyloxy, aryl or hydroxyaryl and wherein said $R^6$ independently is hydrogen or alkyl.

31. A process according to claim 30, wherein said alkyl is linear or branched alkanyl or alkenyl having 1 to 24, such as 3 to 24, 1 to 12, 4 to 12 or 2 to 8, carbon atoms.

32. A process according to claim 28, wherein said orthocarbonate is 3,9-diethyl-3,9-bix(hydroxymethyl)-1,5,7,11-tertraoxaspiro[5.5]undecane.

* * * * *